US007547391B2

(12) United States Patent
Petrie

(10) Patent No.: US 7,547,391 B2
(45) Date of Patent: Jun. 16, 2009

(54) BLOOD IRRADIATION SYSTEM, ASSOCIATED DEVICES AND METHODS FOR IRRADIATING BLOOD

(75) Inventor: Thomas R. Petrie, Newfoundland, NJ (US)

(73) Assignee: Energex Systems, Inc., Emerson, NY (US)

( * ) Notice: Subject to any disclaimer, the term of this patent is extended or adjusted under 35 U.S.C. 154(b) by 316 days.

(21) Appl. No.: 11/285,959

(22) Filed: Nov. 22, 2005

(65) Prior Publication Data

US 2006/0157426 A1 Jul. 20, 2006

Related U.S. Application Data

(60) Provisional application No. 60/630,503, filed on Nov. 22, 2004, provisional application No. 60/638,286, filed on Dec. 21, 2004.

(51) Int. Cl.
*A61L 2/10* (2006.01)
*C02F 1/32* (2006.01)
*A61M 1/36* (2006.01)

(52) U.S. Cl. ................ 210/198.1; 250/438; 250/504 R; 604/6.08; 607/94; 362/321

(58) Field of Classification Search ................. 210/748, 210/198.1, 205; 250/432 R, 435, 437, 438, 250/503.1, 504 R, 504 H; 422/186.3, 24; 604/6.08; 607/94; 362/257, 319, 321
See application file for complete search history.

(56) References Cited

U.S. PATENT DOCUMENTS 1,683,877 A * 9/1928 Edblom et al. ................ 607/92
2,309,124 A * 1/1943 Knott ......................... 250/437
4,463,746 A * 8/1984 Knuth et al. .............. 126/25 R
5,133,932 A * 7/1992 Gunn et al. ................... 422/24
5,660,719 A * 8/1997 Kurtz et al. ................... 210/85
5,712,698 A * 1/1998 Poschenrieder et al. ....... 355/71
6,312,593 B1 11/2001 Petrie ......................... 210/205
7,105,093 B2 * 9/2006 de Gheldere et al. ........ 210/668

(Continued)

FOREIGN PATENT DOCUMENTS

DE 20 2004 004263 5/2004

(Continued)

OTHER PUBLICATIONS

Partial International Search Report dated Apr. 7, 2006 corresponding to PCT/US2005/042427 filed Nov. 22, 2005.

*Primary Examiner*—Frank M Lawrence
(74) *Attorney, Agent, or Firm*—Mintz, Levin, Cohn, Ferris, Glovsky and Popeo PC

(57) ABSTRACT

Embodiments of the present application are directed to devices, systems and methods for irradiating fluids (e.g., blood) with ultraviolet light, and corresponding related components, systems and methods. In some embodiments of the invention, an ultraviolet blood irradiation (UBI) system is provided and may include an ultraviolet UV source providing a predetermined wavelength of radiation to provide a detrimental effect to virus and/or bacteria, an exposure chamber for exposing a predetermined volume of blood to radiation, a conduit between the UV source and the exposure chamber, a pump for pumping blood between a first location and a second location and a shutter assembly provided between the UV source and the exposure chamber providing time-metered irradiation of the blood in the chamber.

31 Claims, 14 Drawing Sheets

16 44 38 40 34 20 24 32 22 42 36 26 28 30

U.S. PATENT DOCUMENTS

2003/0086817 A1 * 5/2003 Horton, III .................. 422/24

FOREIGN PATENT DOCUMENTS

| | | | |
|---|---|---|---|
| EP | 0 638 838 | A | 2/1995 |
| GB | 574 803 | A | 1/1946 |
| WO | WO 98/22150 | A | 5/1998 |
| WO | WO 00/74806 | A | 12/2000 |

* cited by examiner

Counts
2250
1750
1250
750
250
190
290
390
490
590
690
Wavelength (nm)

20
24
22
30
28
32
26
34
36
16
40
38
42
44

78
88
76
80
72
74
84a
90
86a
82
84b
86b
90

106
107
142
130
140
138
72
132
132
60
84b
86b

BLOOD IRRADIATION SYSTEM, ASSOCIATED DEVICES AND METHODS FOR IRRADIATING BLOOD

CLAIM TO PRIORITY AND CROSS-REFERENCED APPLICATIONS

The present application claims priority under 35 U.S.C. §119(e) to U.S. provisional application Nos. 60/630,503, filed Nov. 22, 2004 and Ser. No. 60/638,286, filed Dec. 21, 2004. The subject application is related to issued U.S. Pat. No. 6,312,593, having been invented by the Applicant of the subject application. Each of the foregoing disclosures are herein incorporated by reference in their entirety.

FIELD OF THE INVENTION

Embodiments of the present invention are directed to devices, systems and methods for irradiating fluids (e.g., blood) with ultraviolet light, and corresponding related components, systems and methods.

BACKGROUND OF THE INVENTION

It has long been recognized and understood that specific wavelengths of ultraviolet radiation have the ability to destroy certain biological and chemical structures. While the sun and most active celestial bodies normally emit all types of UV radiation, portions of the earth's atmosphere prevent its destructive form of energy from reaching the surface.

During the last century, scientists and medical practitioners experimented with the use of UV radiation in the treatment of diseases. One such experiment in the late 1930's involved the development of a rudimentary device designed to expose human blood to a UV lamp, in an effort to kill virus and bacteria. This particular device, while medically successful with respect to the patients being treated, was an electrical and mechanical failure due to several factors. First and foremost, the UV lamp was difficult to operate; just to get the lamp to strike was a major handling problem. There were numerous interactive controls that required constant re-adjustment to keep the device operating properly. In addition, the lamp had only a short lifespan before it either failed to strike, or produce the necessary therapeutic wavelength of UV. There was also an ongoing general maintenance issue with a water cooling process and a belt drive sequence of included mechanics. In addition, the control of the flow rate of the blood through the system also required constant adjustment and monitoring by a trained operator. Because of the design of the device, blood collection was also difficult. Specifically, gravity was used to draw and collect the blood into an open beaker. The beaker was than moved to a position above the device and allowed to drain through the pump and exposure chamber.

Although positive therapeutic treatments resulted when all system components were operating properly, such conditions did not occur often. Moreover, if a mechanical, electrical or lamp problem developed during the course of a clinical procedure, the system provided no visual or audible indications to notify the operator or an automatic fail-safe termination of operation.

SUMMARY OF THE INVENTION

Accordingly, in response to the problems of such prior art systems and devices for blood irradiation, embodiments of the present invention are provided. While preferred embodiments of the present invention utilize the same fundamental principal to irradiate blood, such embodiments provide a dramatically improved system and process. In some embodiments, the system automatically controls and monitors the blood irradiation process. Moreover, embodiments of the present invention may include established clinical parameters to ensure a safe and therapeutically effective medical procedure.

Accordingly, in one embodiment of the present invention, a blood irradiation system is provided and may include an ultraviolet UV source providing a predetermined wavelength of radiation to provide a detrimental effect to virus and/or bacteria, an exposure chamber for exposing a volume of blood to radiation, a conduit between the UV source and the exposure chamber, a pump for pumping blood between a first location and a second location and a shutter assembly provided between the UV source and the exposure chamber providing time-metered irradiation of the blood in the chamber.

In another embodiment of the present invention, a blood irradiation system is provided and may include an ultraviolet UV source providing a predetermined wavelength of radiation to provide a detrimental effect to virus and/or bacteria, an exposure chamber for exposing a volume of blood to radiation including one or more protuberances to impart a particular fluidic turbulence upon a flow of blood within the chamber, a conduit between the UV source and the exposure chamber, a pump for pumping blood between a first location and a second location and a shutter assembly provided between the UV source and the exposure chamber providing time-metered irradiation of the blood in the chamber. The shutter assembly includes a first shutter having a fixed open position and a fixed closed position and a second shutter which is repeatedly opened and closed according to a predetermined timing. The system may also include a cooling plenum comprising an air inlet, a filter, a duct, a fan and an outlet, a control system for controlling operation of the system and at least one thermal sensor comprising a thermal circuit breaker for controlling power supply to the ultraviolet radiation source.

In another embodiment of the invention, a shutter assembly for a blood processing system is provided and may include a rotating disc having one or more spaced apart openings. Each of the openings capable of being rotated to correspond to at least a portion of a first aperture in a fixed open position such that upon the first aperture being in an open position. UV radiation may pass through the shutter upon one of the openings of the one or more openings of the disc aligning with the open position of the first aperture.

In another embodiment of the invention, a method for irradiating blood is provided and may include flowing a predetermined volume of blood through the exposure chamber and alternately exposing the flow of blood to UV radiation via a moving shutter, such that the flow of blood is exposed to the radiation according to a predetermined timing.

In another embodiment of the present invention, an administration set for collecting a predetermined volume of blood from a patient is provided and may include a collection vessel having a predetermined pressure below atmospheric, a first needle for inserting into the collection vessel, a reservoir bag capable of performing as a conduit under atmospheric pressure and performing as a reservoir at or above atmospheric pressure and a second needle for insertion into a patient.

In yet another embodiment of the invention, a container for passing and/or containing blood is provided and may include a container and a tube. The tube may include a first port provided in a first position for transporting blood to or from the bag, a second port having an associated valve, the second port being located at a second position slightly higher vertically than the first position, and a third port provided in a third position higher vertically than the first position and the second position. The valve closes upon application of a pressure to the first and/or third ports which is lower than atmospheric and opens upon application of a pressure to the first and/or third ports of atmospheric or greater.

These and other embodiments, features, advantages and objects of the invention will become even more apparent with reference to the following detailed description and attached drawings, a brief description of which is set out below.

DETAILED DESCRIPTION OF THE EMBODIMENTS

FIGS. 1-17 illustrate some of the embodiments of the present invention. To that end, some of the figures illustrate an Ultraviolet Blood Irradiation (UBI) system (also referred to as a "Hemo-Modulator") which includes specifically arranged mechanical and electronic components to provide a well-defined exposure of patient blood to UV radiation. According to some embodiments of the present invention, such mechanical and electrical components may include an ultraviolet (UV) lamp, a fluid pump, an exposure chamber, and control logic means. Such embodiments may also include a variety of sensory items for monitoring and carrying out irradiation and other operation processes.

Figure 1:
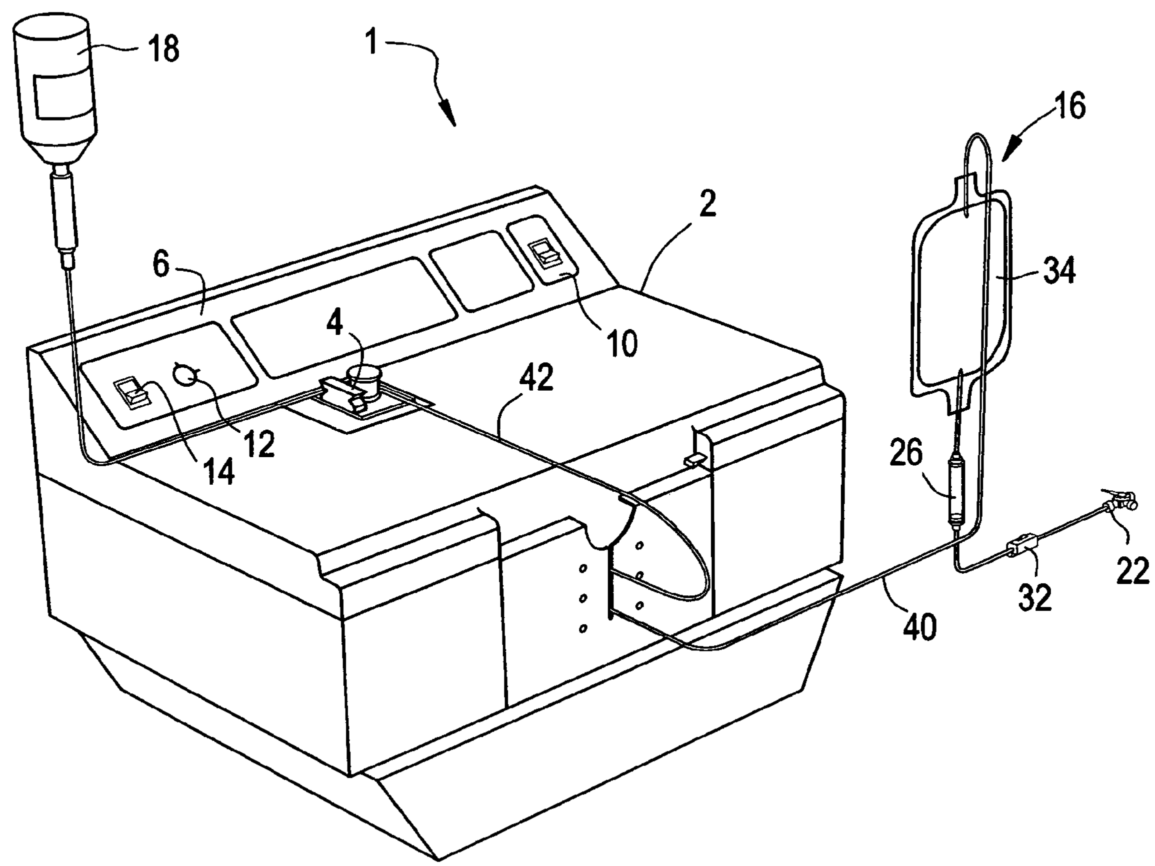
FIG. 1 is a perspective view of a blood irradiation system according to some of the embodiments of the present invention.

FIG. 1 illustrates one embodiment of the present invention directed to a UBI system for irradiating blood (or other fluid). As shown, the system 1 is housed in a convenient cabinet 2, which may be provided as a table-top unit or may include structure with wheels (i.e., a cart), such that the cabinet/system may be easily transported. Mounted on the cabinet may be a pump 4, control panel 6 and a receiving portion/housing for receiving a blood exposure chamber of an administration set (described below).

The control panel may include controls, including, for example, a switch for main power 10, UV lamp switch 12 (preferably a keyed switch), and pump switch 14. Each switch may also include one or more corresponding LED lights for indicating a status of the associated mechanism (e.g., main power "on/off"). For example, the main power switch may include a red LED which is lit when the switch is in the on position. Similarly, the UV lamp switch preferably includes a series of associated LEDs for indicating a "warm-up" condition (UV lamp warming up to operating condition). For example, in a short time (e.g., between about 30-120 seconds, preferably around 90 seconds) a red LED may be lit upon initial lamp turn-on (indicating that the lamp is not yet ready to irradiate blood) which may then turn off upon the lamp reaching an operating condition—at that point, a green LED may be lit (or the red LED may change to green) indicating that the UV lamp is ready to irradiate blood. To ensure a long lifespan of the UV lamp, the lamp preferably is turned on and off as little as possible. Thus, if a plurality of patients require treatment, the UV lamp preferably remains "on" the entire time (e.g., left "on" between individual blood irradiations).

Figure 2:
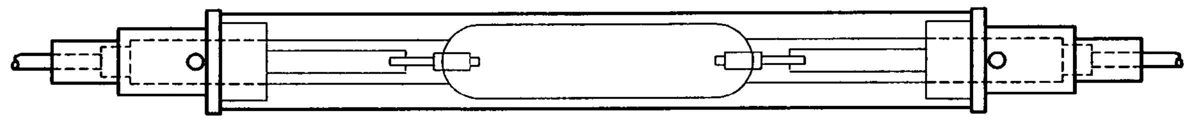
FIG. 2 is a side view of an exemplary UV source (e.g., lamp/bulb) according to some of the embodiments of the present invention.
Figure 3:
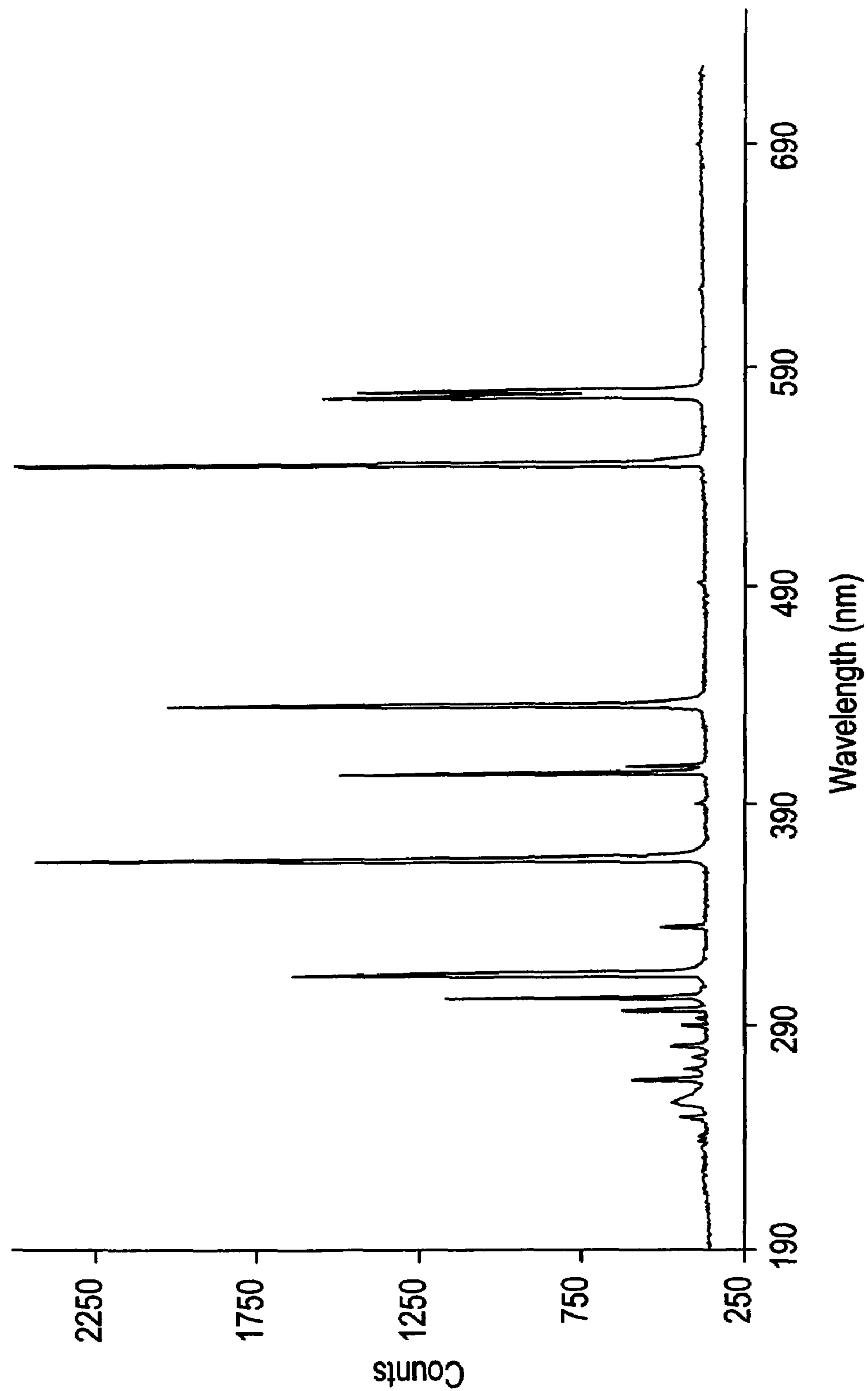
FIG. 3 is a spectral output of a UV source used in some embodiments of the present invention.

The UV lamp preferably provides a specific wavelength of radiation known to be clinically effective in destroying or substantially destroying virus and/or bacteria. Such wavelengths may be between 200-400 nm, to treat, for example, human immunodeficiency virus (HIV-1, HIV-2), autoimmunodificiency syndrome (AIDS) in human and animal whole blood, blood products and process blood components. The UV lamp may be encased in a glass tube to stabilize and maintain proper operating temperature and eliminate any foreign matter contact. While in one embodiment of the invention, the UV lamp may comprise a 210 watt medium pressure mercury vapor lamp, having 2.0" arc, an overall length of about 8.5 inches and a width of about 1.0 inch, other types of UV lamps of different wattages, lengths, widths and arcs may be used. One of skill in the art will appreciate that a change in the bulb, to a different type. FIG. 2 represents a side view of one type/size of UV lamp that may be used in embodiments of the present invention. FIG. 3 represents the relative spectral and energy output of such a lamp.

Pump 4 is used to flow blood, at predetermined flow rates, through the exposure chamber, and preferably in both directions. In preferred embodiments, the pump comprises a peristaltic pump, although other types of pumps may be used. The flow rate of the pump may depend on an assortment of variables including UV lamp strength, exposure chamber design and/or volume, and the size/diameter of the tubing/conduit (i.e., PVC or silicon tubing) which transports the blood to and from the pump and/or exposure chamber. The pump fluid flow rate is preferably is set to a predetermined calibrated flow, but some embodiments of the invention may include controls as to adjust the flow rate to a number of settings. Typically, the predetermined set flow rate may be routinely checked to ensure proper operation of the system. Such inspection may be accomplished via a visual flow indicator (e.g., flow gauge). Commercially available flow rate sensors may be included to monitor the flow rate and initiate a shut down of the system upon the rate varying greater than a predetermined amount (e.g., plus or minus 5 percent of the ideal flow rate). Such monitoring may be effected by an electrical/computer control system (for example).

FIG. 1 also illustrates the UBI system with administration set 16 connected thereto. According to some embodiments of the invention, the administration set is a single-use, disposable system. This ensures that blood from one patient does not mix with blood from another patient, and allows the system to operate inexpensively and effectively. As shown, blood from a patient is collected in a collection reservoir 18 (IV bottle/bag). A portion of tubing of the administration set is placed in the peristaltic pump so that the pump can act on the tubing to create a pumping pressure in one or preferably both directions, depending upon whether blood is being sent to or from the reservoir container.

Figure 4:
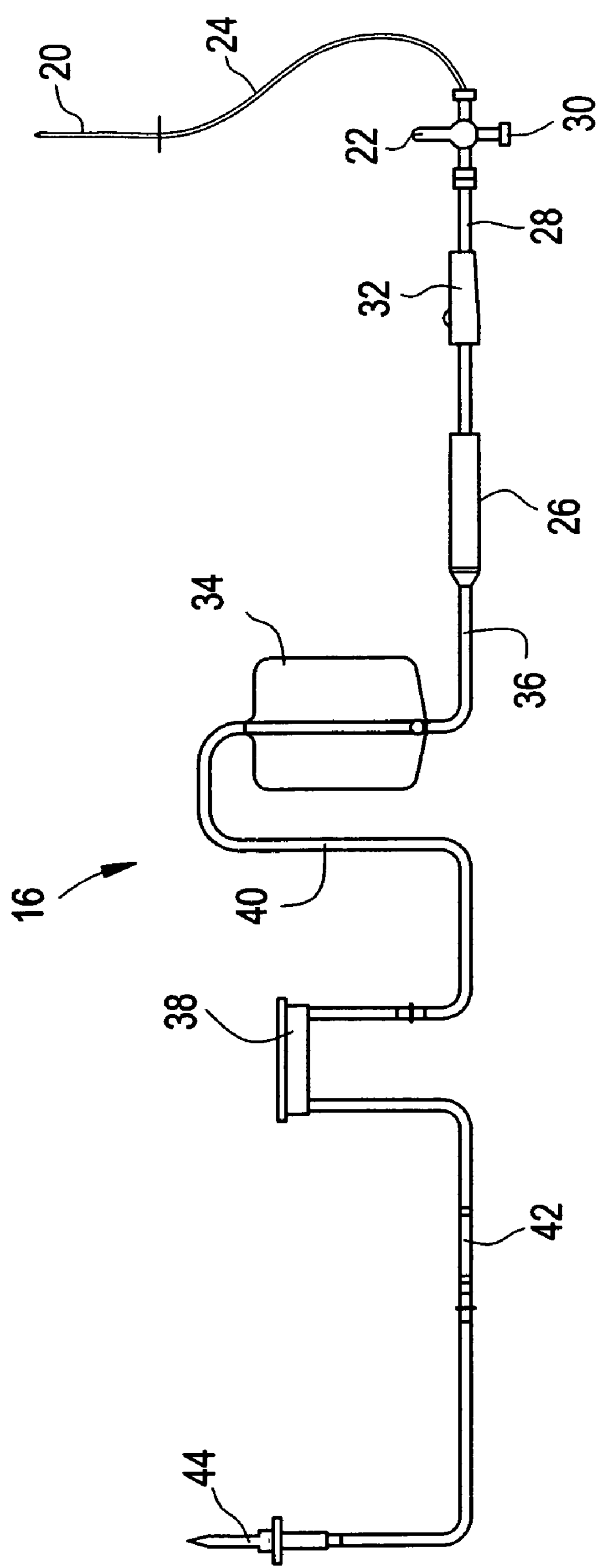
FIG. 4 is a schematic side view of an administration set according to some embodiments of the present invention.

As shown in FIG. 4, some preferred embodiments of the systems administration set include a needle 20 for insertion into a patient for collecting and infusing blood, this may be directly connected to a three-way stopcock 22, or a length of PVC/silicon tubing 24 may connect the stopcock and needle. The stopcock is connected to a drip-tube via PVC tubing 28. The three-way stopcock may include a port for transfer of fluids to a patient (patient port) being connected to a patient needle, another port 30 for a syringe (syringe port) and the third port for communicating fluids to/from the system. Along the PVC tubing connecting the stopcock to the drip-tube may be a roller clamp 32 (or other clamp) to stop flow of blood to/from the patient. The drip-tube may then be connected to a soft walled venous reservoir 34 via a length of PVC tubing 36, which may then be connected to one side of exposure chamber 38 (see also, FIG. 5) via PVC tubing 40.

A length of silicone tubing 42 (which may be used in combination with the peristaltic pump) is connected from the other side of the exposure chamber to a blood spike 44 for insertion into an IV bottle (vacuum bottle; e.g., Vac Bottle 500 ml by McGaw). While silicone tubing may be used along the entire length from the UV exposure chamber to the blood spike, PVC tubing may be used as well or a combination thereof.

Figure 6:
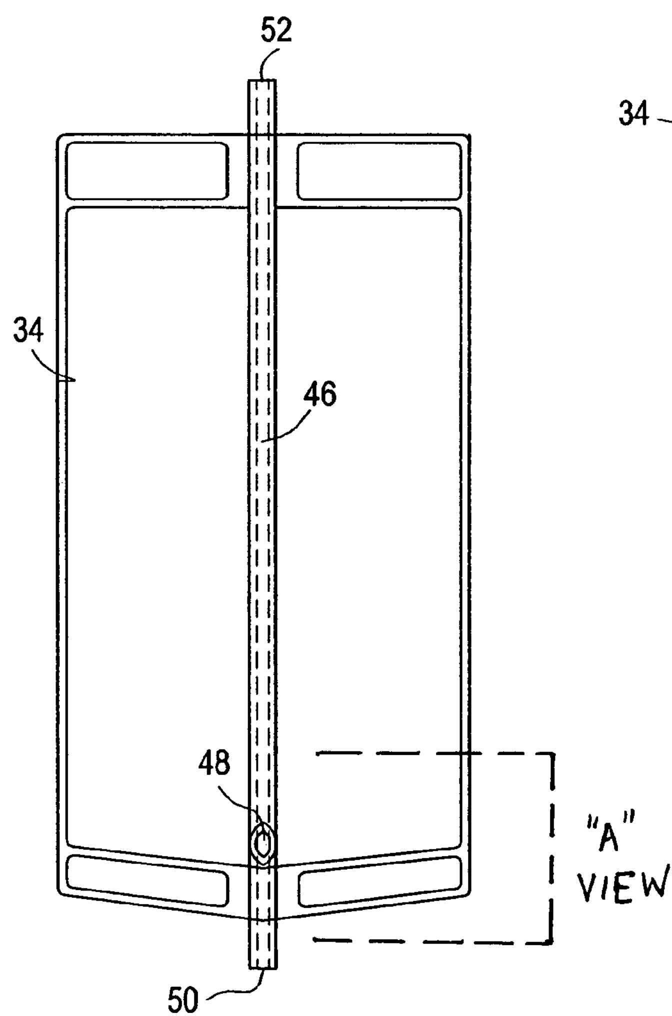
FIG. 6 is a front view of a reservoir/flow-through bag according to some of the embodiments of the present invention.
Figure 7:
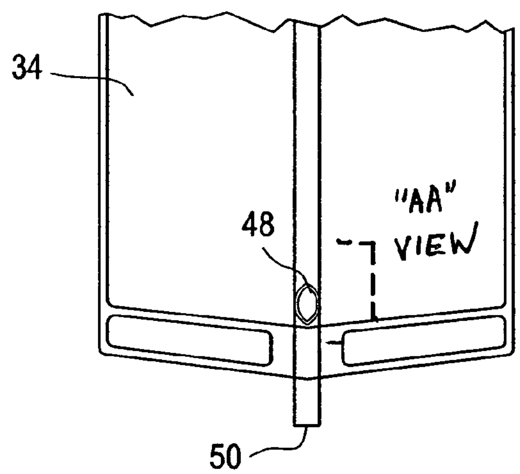
FIG. 7 is an enlarged portion "A", as depicted in FIG. 6, of the reservoir/flow-through bag.
Figure 8:
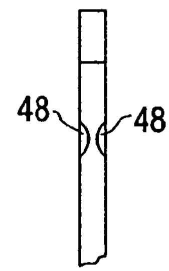
FIG. 8 is an enlarged portion "AA", as depicted in FIG. 7, of the reservoir/flow-through bag.

The soft wall venous reservoir bag 34 is shown in FIG. 6-8. In some embodiments of the present invention, the soft wall bag preferably includes a plastic tube 46, within the bag, having sufficient stiffness as to not collapse upon a vacuum being applied to the tube. The tube 46 preferably includes an opening 48 (or a plurality of such openings) at a base position of the bag 34, near a first opening 50 of the tube for ferrying liquids through the tube. A second opening 52 located at an opposite end of the tube may also be provided for ferrying liquids through the tube. Upon a vacuum (i.e., a lower pressure) being applied to the bag, a portion of a wall(s) of the bag collapses onto opening 48, which allows fluid to flow through tube 46 in the direction of the lower pressure—i.e., if a vacuum is being applied at opening 52, fluid flows from opening 50 to opening 52; if a vacuum is being applied at opening 50, then the flow is the reverse. The bag may also act as a reservoir (i.e., fill with a fluid) for a fluid being ferried (e.g., blood) upon a normal (e.g., around atmospheric) or positive pressure being applied to the bag. Thus, opening 48, in combination with the bag, operates as a valve depending upon whether positive or negative pressure is supplied to the bag.

Other embodiments of the venous reservoir bag may include a hard-walled bag which includes a tube having a valve provided at a base portion of the tube. Contrary to the embodiments described immediately above, in these embodiments, the opening at the base of the tube does not require a wall(s) of the bag to cover the hole when a negative pressure is applied to the tube. Instead, a mechanical valve located proximate the opening in the tube opens and closes the opening based on a positive (open position) or negative (closed position) pressure. Such a mechanical valve may simply comprise a "flap" of plastic (e.g., thin sheet of plastic) affixed to or near a side of the opening which, upon a negative pressure, the flap covers and substantially seals the opening, and upon a positive pressure, fluids/blood can pass through the opening to be stored (e.g., temporarily) in the bag. Other types of valves may also be used, including, for example, a ball-in-cage valve.

Accordingly, the bag performs as a conduit when a vacuum is applied when a patient's blood is being drawn and as a reservoir to collect the blood volume difference between a treatment flow rate and the patient site return rate, when blood (treated or untreated) is re-infused into the patient. Accordingly, in some embodiments of the invention, the design of bag 34 minimizes hemolysis in either flow direction and allows collection of returning blood in a bulk format. For operator convenience, the bag may include a volume indication on one or both sidewalls and the bag may be used in conjunction with the treatment of whole blood or blood products.

The drip tube 26 of the administration set may be used to regulate the flow rate being applied by the vacuum and needle bore during blood collection or regulate flow for blood re-infused into a patient. The vacuum pressure may be established via a vacuum being present in the vacuum bottle (which is then transferred to the bag 34 upon blood spike 44 being inserted into the vacuum bottle), or any other way (e.g., via the pump or syringe). In some embodiments of the invention, a typical draw flow rate is approx. 25-30 ml per minute and a typical flow return rate is preferably about 10-20 ml per minute. Generally, the draw of blood from a patient may vary depending on the patient.

Typically, re-infusion flow rates are generally limited to approximately the flow rate(s) disclosed above (or similar flow rates disclosed in the prior art and/or familiar to those of skill in the art). Higher re-infusion flow rates can cause a great deal of discomfort. The re-infusion rate of blood may be regulated by an operator/doctor/nurse using a visual indication of the drip tube (for example) and an IV valve. In most cases, the irradiation process is preferably completed before all the blood is returned to the patient. To that end, the reservoir bag allows the patient to be removed from the UBI system and relax at another location while the rest of the patient's irradiated blood is returned to the patient. This frees the UBI system to perform additional treatments on other patients. In some embodiments, if managed properly, the one patient/treatment may be effected about every 12 minutes. This time may be shorter or longer depending upon flow and draw rates, and rates of irradiation (e.g., upon different diameter tubes being used, upon different dosages of radiation, and the like).

Prior to blood being returned to the patient after irradiation, the vacuum may be vented to the atmosphere. This may be done via the stopcock or any other way familiar to those of skill in the art. Accordingly, the loss of vacuum allows the soft walls of the reservoir bag 34 to relax, which allows the returning blood to accumulate/pool in the bag 34 (i.e., performing as a reservoir).

Figure 5:
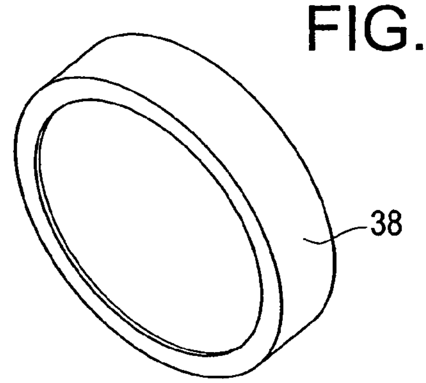
FIG. 5 is a perspective view of an exposure chamber according to some of the embodiments of the present invention.

The exposure chamber 38, one embodiment of which is illustrated in FIG. 5, may also be considered part of the administration set (and thus is also preferably a single-use, disposable unit), or may be considered a separate component thereof. The exposure chamber may include two openings, which allows blood to flow from one side of the device to the other, and also preferably allows the chamber to be substantially filled with blood. The chamber preferably includes one or more protuberances to cause fluidic turbulence to the blood flow. The turbulence to the blood flow allows a more complete exposure to the UV radiation source. The exposure chamber may also include a quartz cover on one side (e.g., a side being exposed to the UV radiation), which is preferably transparent to UV in the range of about 1400 to about 4000 Angstroms or between about 140 to about 400 nm. The chamber is preferably disposable, and thus, is preferably designed for easy installation and removal from the system. An example of such a chamber may be found in issued U.S. Pat. No. 6,312,593, to Petrie, the entire disclosure of which is herein incorporated by reference.

Figure 9:
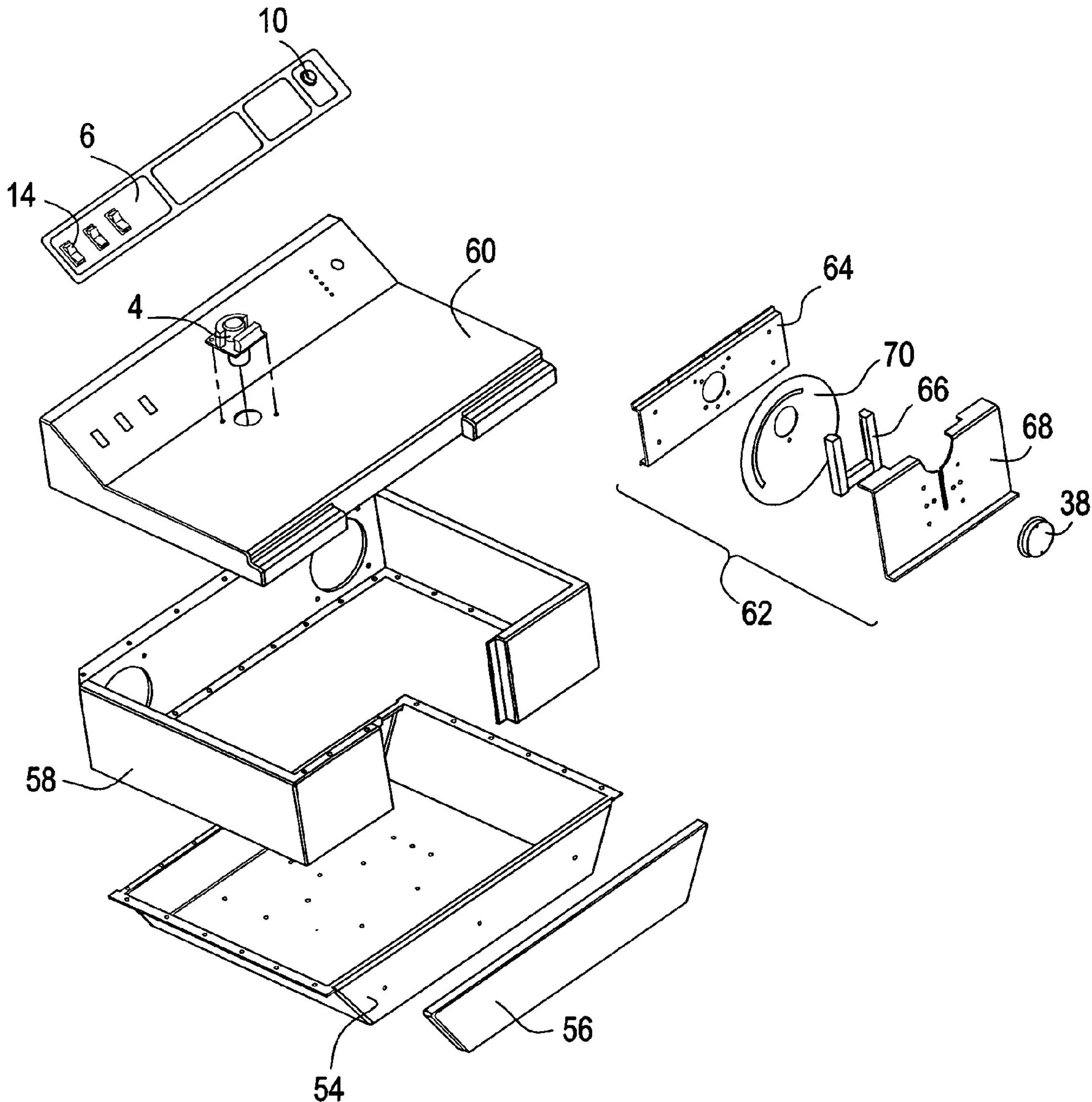
FIG. 9 is an exploded perspective view of a blood irradiation system according to some embodiments of the present invention.

FIG. 9 illustrates an exploded perspective view of the UBI system according to some embodiments of the present invention. As shown, the cabinet 2 may include a cabinet base 54, a front bumper 56, a middle wrap 58 and a cover 60. Pump 4 and control panel 6 may also be seen in this figure, as well as an exposure chamber housing assembly to house an exposure chamber 38. The exposure chamber housing may include a chamber mount 64, a shutter assembly 62, a chamber bracket 66, and a front panel 68.

Figure 10:
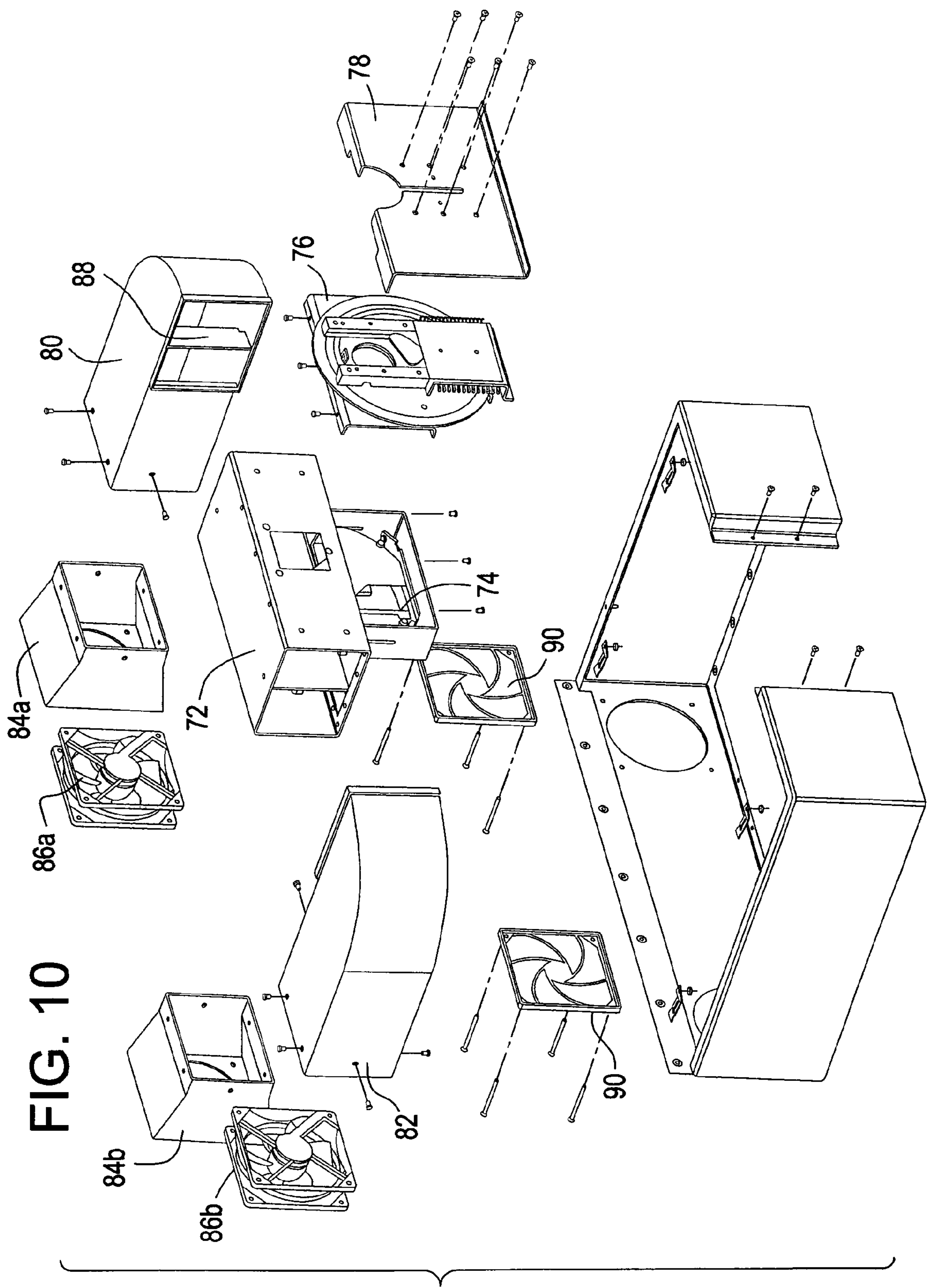
FIG. 10 is an exploded perspective view of an interior portion of a blood irradiation system according to some embodiments of the present invention.
Figure 12:
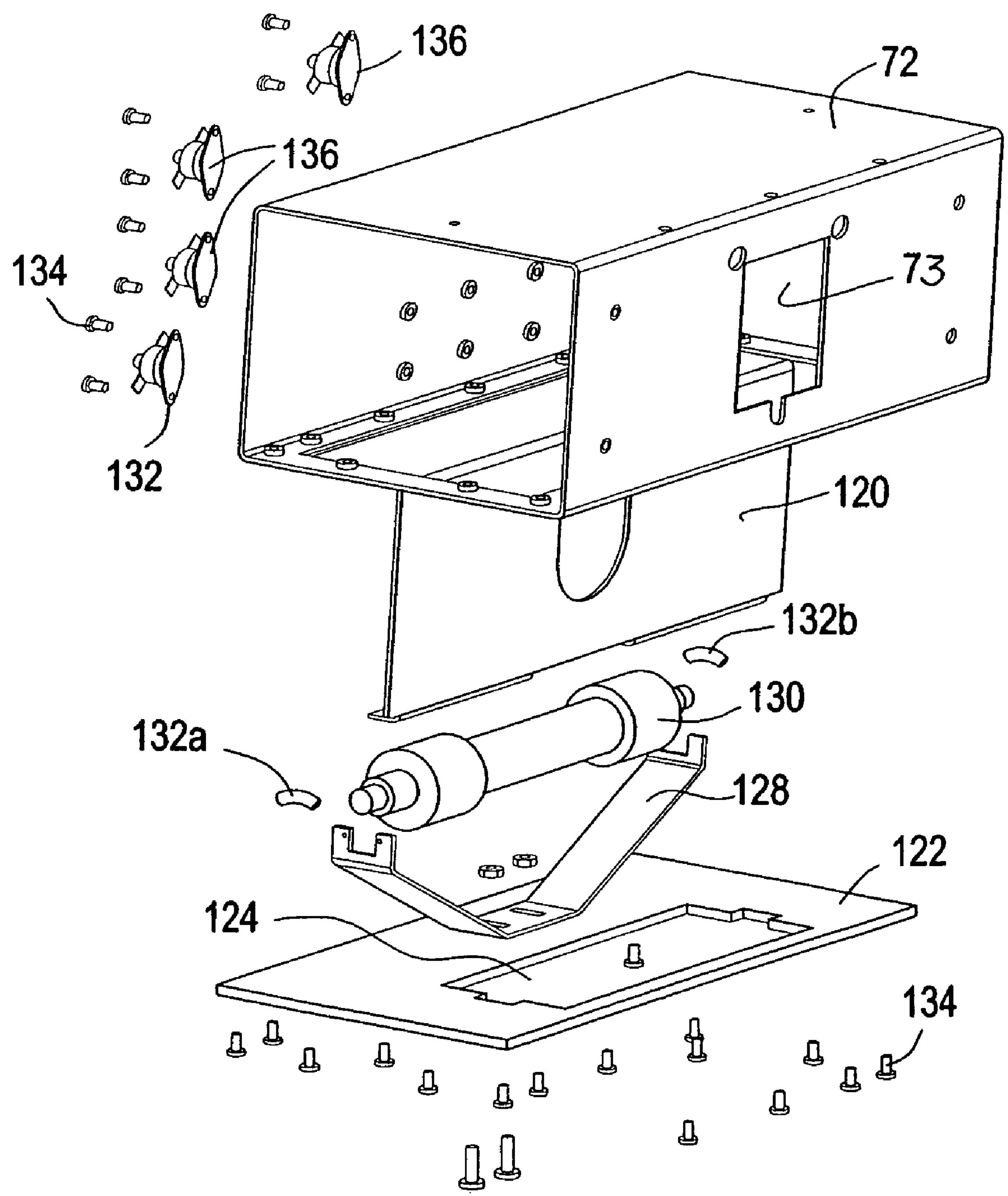
FIG. 12 is an exploded perspective view of a UV lamp housing according to some embodiments of the present invention.
Figure 13:
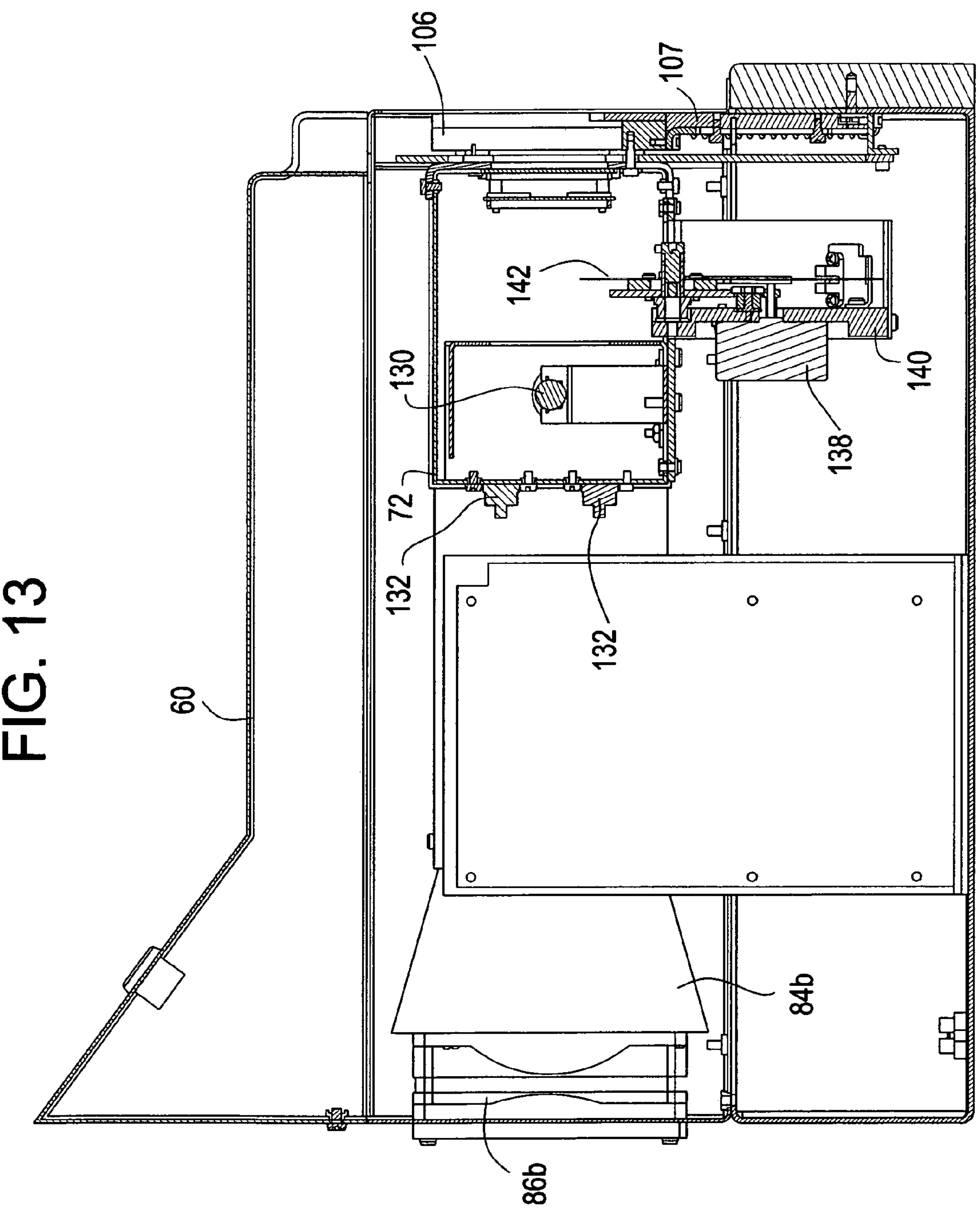
FIG. 13 is a side, cross-sectional view of a blood irradiation system according to some embodiments of the present invention.

FIG. 10 is an exploded perspective view of the components housed in the center wrap section of the UBI system according to some embodiments of the present invention. Reference is also made to FIGS. 11-13. As shown, housed in the middle wrap section may be a UV lamp housing 72 (which houses the UV lamp), chopper-wheel assembly 74 and shutter assembly 76, which also includes front panel 78. Preferably, the UV lamp housing is provided with an air cooling plenum, or is part of an air cooling plenum, which may be provided in the center wrap section. The plenum may be used to or aid in maintaining a proper temperature in the space local to the UV lamp so that the UV lamp does not overheat (causing shutdown to the system). Such a plenum may include ducts 80 and 82, each respectively connected to a duct end/shroud 84*a, b*.

Between each shroud (or at least one of the shrouds) and a respective duct may be a fan unit 86*a, b* (although the fan may be located in other areas of the middle wrap section or other portion of the cabinet/UBI system). Each duct may include a deflector 88, to deflect all or a portion of the airflow in a predetermined direction, and/or to split the airflow. As shown in the figure, the deflector may be positioned in the center of the opening of the end of the duct which is connected to the UV lamp housing, so that the lamp receives a portion of the airflow and the chopper-wheel mechanism receives a portion. A filter 90*a, b* is preferably at the end of one or both of the shrouds (depending upon airflow direction). Preferably, the filters are replaceable, and conveniently positioned on a portion of the cabinet which is easily accessible (for ease of replacement).

Airflow through the UV lamp assembly may be in one direction, flowing into shroud 84*a* pushed by fan 86*a*, and exiting out shroud 84*b* (pulled by fan 86*b*). Alternatively, the flow of air may be into the UV lamp housing from both ducts; that is, fan 86*a* and fan 86*b* both draw air into each shroud, and each duct directs the air into the UV lamp housing. In the later case, a vent may be provided which allows air to vent out of the interior of at least one of the UBI system (as a whole), the lamp housing and the middle wrap section.

Figure 11A:
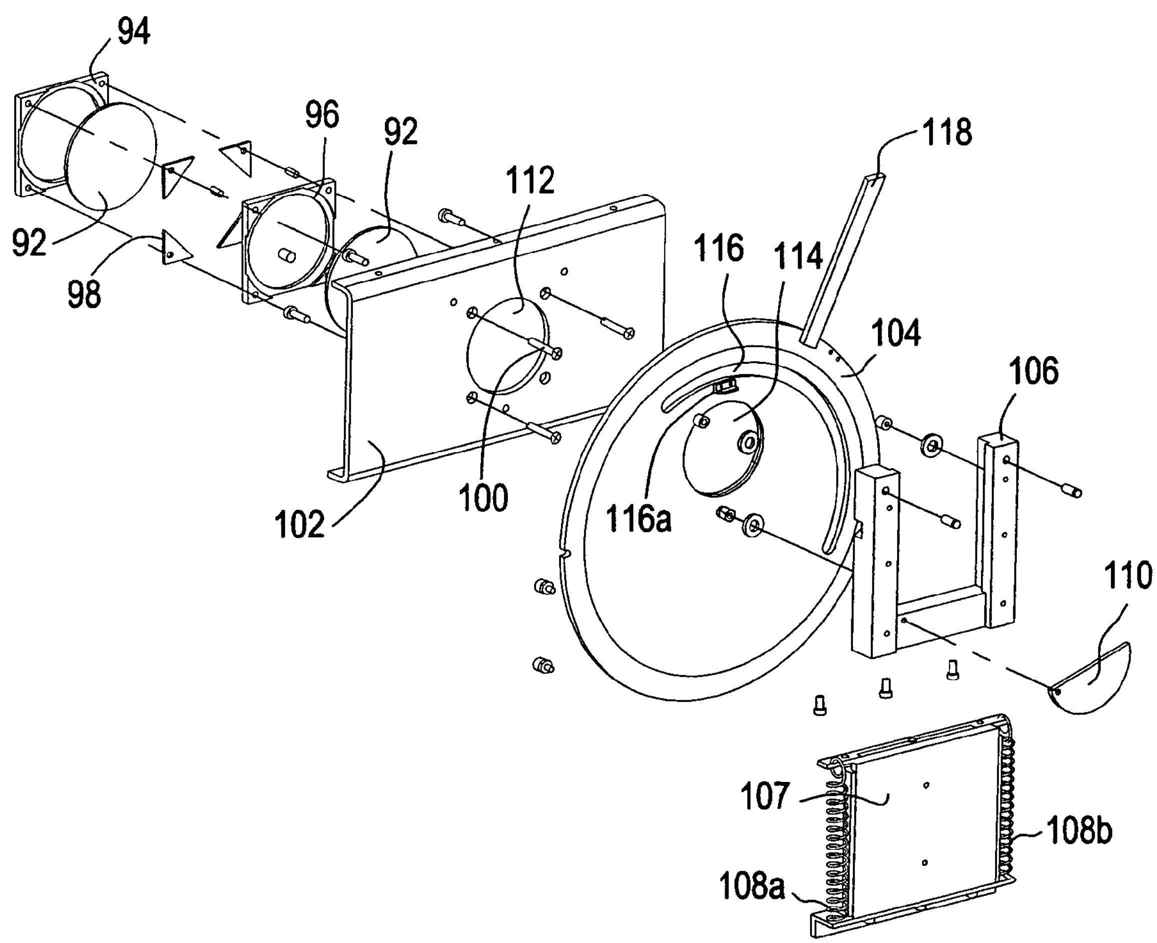
FIG. 11A is an exploded perspective view of a shutter assembly according to some embodiments of the present invention.
Figure 11B:
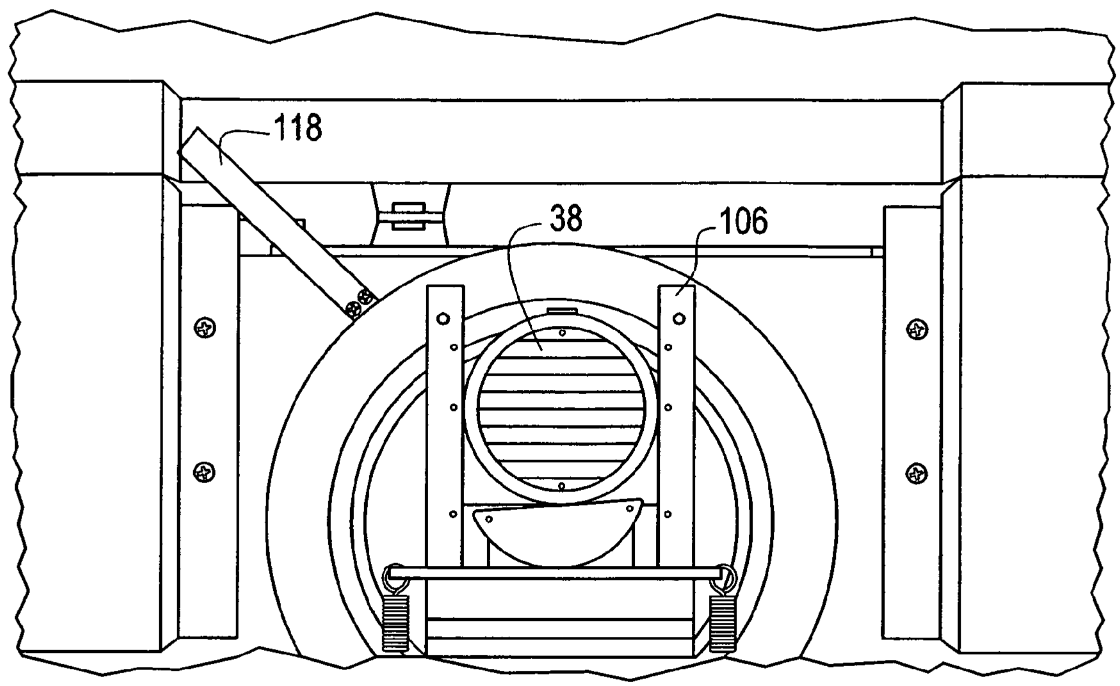
FIG. 11B is a front view of the shutter assembly, having an exposure chamber included therein, in a "closed" position.
Figure 11C:
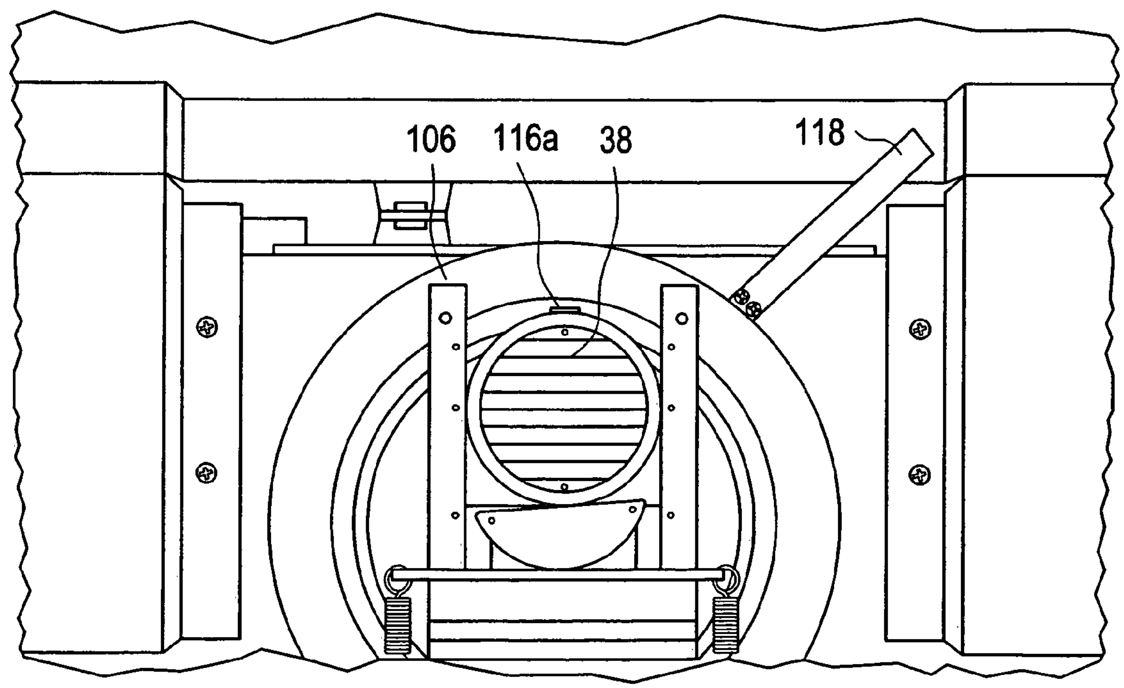
FIG. 11C is a front view of the shutter assembly, having an exposure chamber included therein, in an "open" position.

FIG. 11A illustrates an exploded view of the shutter assembly according to some embodiments of the present invention, which controls whether UV radiation is provided to the exposure chamber. The shutter assembly may include filter(s) 92, which may be used to filter out specific wavelength of the electromagnetic spectrum, and may be housed by filter brackets 94 and 96 (as well as other structure, e.g., clips 98 and fasteners 100). The shutter assembly may also include a chamber mounting plate 102, shutter plate assembly 104, chamber bracket 106, chamber lock assembly 107 (having springs 108*a, b*) and cell release cam 110. The chamber bracket is slidably connected to the chamber lock assembly, and the top of springs 108*a, b* attach to the bottom of the chamber bracket and the bottom of the springs are attached to the bottom of the chamber lock assembly.

The chamber mounting plate includes an opening 112, for allowing UV radiation to pass. The shutter plate assembly may include a corresponding opening 114 to allow the radiation received via opening 112 in the chamber mounting plate to pass. The shutter plate assembly may also include an elongated radial arc 116 which is slidably connected to the upper portion of chamber bracket 106.

The shutter plate assembly may also include a cam lever 118 which allows an operator to manually open and close the shutter upon the insertion of or removal of an exposure chamber. It will be appreciated by one of ordinary skill in the art, that such manual operation may be replaced by a servo or other mechanical or electromechanical device, which opens and closes the shutter according to operational parameters and/or switches located on the control panel (or located adjacent to the shutter assembly). Insertion of the chamber into the chamber receiving window results in the exposure chamber being pushed down (by the operator, for example) to release the locking cam. The cam lever may then be moved from right to left to lock the chamber into position and, in some embodiments, at the same time the exposure window is opened.

In some embodiments, movement of the cam lever 118 causes protrusion 116*a* to contact the upper portion of an exposure chamber inserted into the chamber bracket, and ride along an exterior diameter of the exposure chamber while also causing the exposure chamber to be pushed downward. This in turn causes the bottom portion of the exposure chamber to actuate cell release cam 110, which in turn pushes downward on the top portion of the chamber lock assembly. This causes the chamber bracket to rise up relative to the chamber lock assembly (i.e., the springs are stretched), to a maximum point when protrusion 116*a* is in a 12 o'clock position. This occurs when lever is swung to one side ("aperture open" position). To release the exposure chamber, the lever is moved to the opposite side, such that protrusion 116*a* no longer engages the exposure chamber and chamber bracket 106 moves downward.

Accordingly, when lever 118 is in the "open" position (see FIG. 11C; lever 118 swung to a right-side position), the exposure chamber is aligned for proper exposure to the UV radiation and prevents the escape of radiation from the front of the UBI system. When lever 118 is in the "closed" position (see FIG. 11B; lever 118 swung to a left-side position), the exposure chamber may be removed from the UBI system. Thus, movement of lever 118 in one direction or another effects and an open or a closed position: i.e., opening 114 in the shutter plate assembly moves to a position either corresponding to the opening 112 in the chamber mounting plate, or a position in which opening 114 in the shutter plate assembly does not overlap the opening 112 in the chamber mounting plate (of course, other "partial open" positions are possible, depending upon the particular use of the UBI).

A center portion of the shutter plate assembly is preferably made of polybetrafluoroethylene or may also be made of Teflon®, as may other structures of the shutter assembly which are exposed to the UV radiation. The polybetrafluoroethylene is preferable as this material is better able to withstand the repeated exposure to UV radiation, which has a detrimental effect, over time, to many materials.

An exploded perspective view of UV lamp housing 72 is illustrated in FIG. 12. As shown, the lamp housing includes internal light port 120, chopper assembly plate 122 (with opening 124 for allowing chopper wheel (not shown) to pass therethrough), lamp bracket 128, lamp 130, springs 132*a, b*. A plurality of fasteners 134 maybe used to assemble one or more of the components. Upon the air plenum (see above) failing to keep the UV lamp cool, one or more thermally sensitive electrical circuit breakers 136 (e.g., one or more thermisters) may be included to shut down the UV lamp (but preferably keep the air plenum operational). Such thermisters may be located in series on the exterior of a portion of the air plenum across from the UV lamp and may operate to turn the lamp off and prevent any restart if the plenum surface temperature reaches 50° C. (for example). In another exemplary embodiment, the temperature can reach up to 90° C. Such a series wired dual thermistor design may be used as a redundant safety system design for additional protection. These features aid in ensuring a long life, high number of turn-on strikes, and a stable and repeatable ultraviolet wavelength of radiation from the UV lamp.

Figure 14:
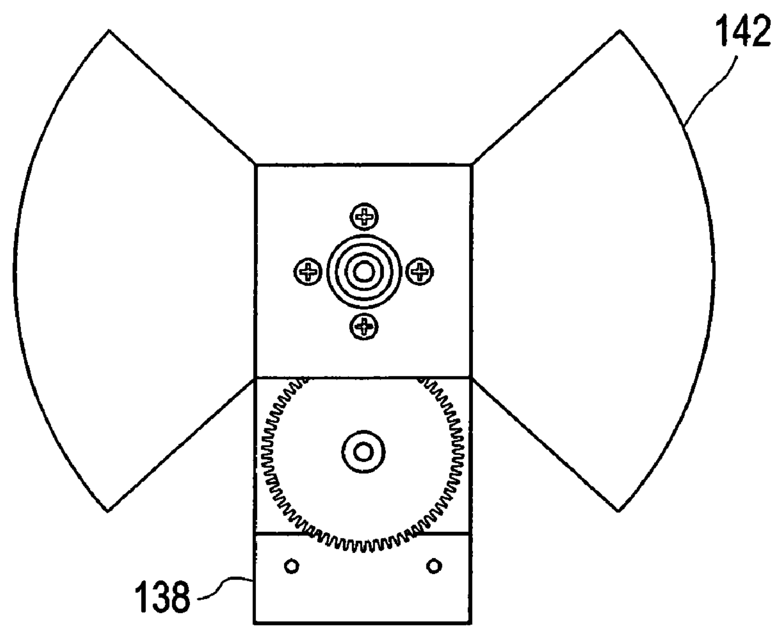
FIG. 14 is a front view of a chopper-wheel assembly according to some embodiments of the present invention.
Figure 15:
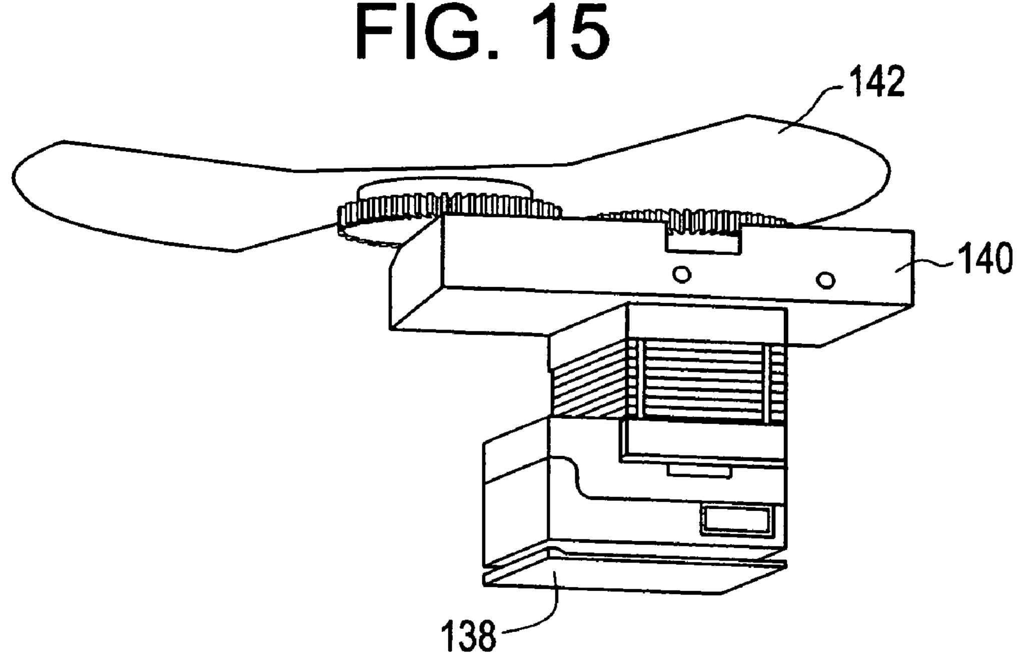
FIG. 15 is a side view of a chopper-wheel assembly according to some embodiments of the present invention.

FIG. 14 illustrates a front view and FIG. 15 a side view of a chopper wheel device according to some embodiments of the present invention. The chopper-wheel device effects a "shutter" effect to the radiation. As shown, the chopper-wheel device may include a motor 138, a mounting bracket/plate 140, and a "bow-tie" disk 142. FIG. 11A illustrates that upon rotation of the bow-tie disk, the shutter effect of UV radiation is produced from the UV lamp—i.e., portions of the bow-tie disk which lack material allow radiation to pass through opening 114, while the remaining portions block radiation. Accordingly, the chopper-wheel mechanism provides a time-metered exposure of the blood in the exposure chamber. Specifically, the chopper wheel provides alternative "open" and "closed" positions of the aperture between the UV lamp and the exposure chamber. The chopper wheel/aperture device timing may be determined by using a particular synchronous motor and gear drive selected for this application. According, due to the specifications of such components, timing is highly accurate and typically only change as a result of a major malfunction. In an embodiment, the chopper device is a belt drive chopper device.

In some embodiments of the present invention, the chopper-wheel assembly preferably includes a parking device which parks the chopper-wheel in a position which substantially blocks radiation-i.e., the solid portion of the chopper-wheel block opening 114. This feature performs as an added safety feature upon shutdown of the system, so that radiation is blocked from being transmitted to the exposure chamber. Thus, during such a system shutdown, the rotating chopper-wheel automatically stops in a position such that none of the opens areas of the chopper-wheel overlap with opening 114 and/or opening 73 of the lamp housing (as shown in FIG. 12).

The UBI system according to some embodiments of the present invention is preferably designed to provide fail-safe electrical and mechanical operation so as to ensure that blood components are not damaged and that the patient is not placed in jeopardy. This may be accomplished by controlling and monitoring various system parameters (as indicated above), which may be necessary in order to ensure a safe and therapeutically effective medical procedure. The control logic may (e.g., electronics-hardware and/or software) categorize the instrument into five (5) functional states: three (3) of which may be operational, an alert state and a fail-safe state. Transition from one state to another may be based upon sensory information obtained from various sensors monitoring the various components of the system.

Figure 16:
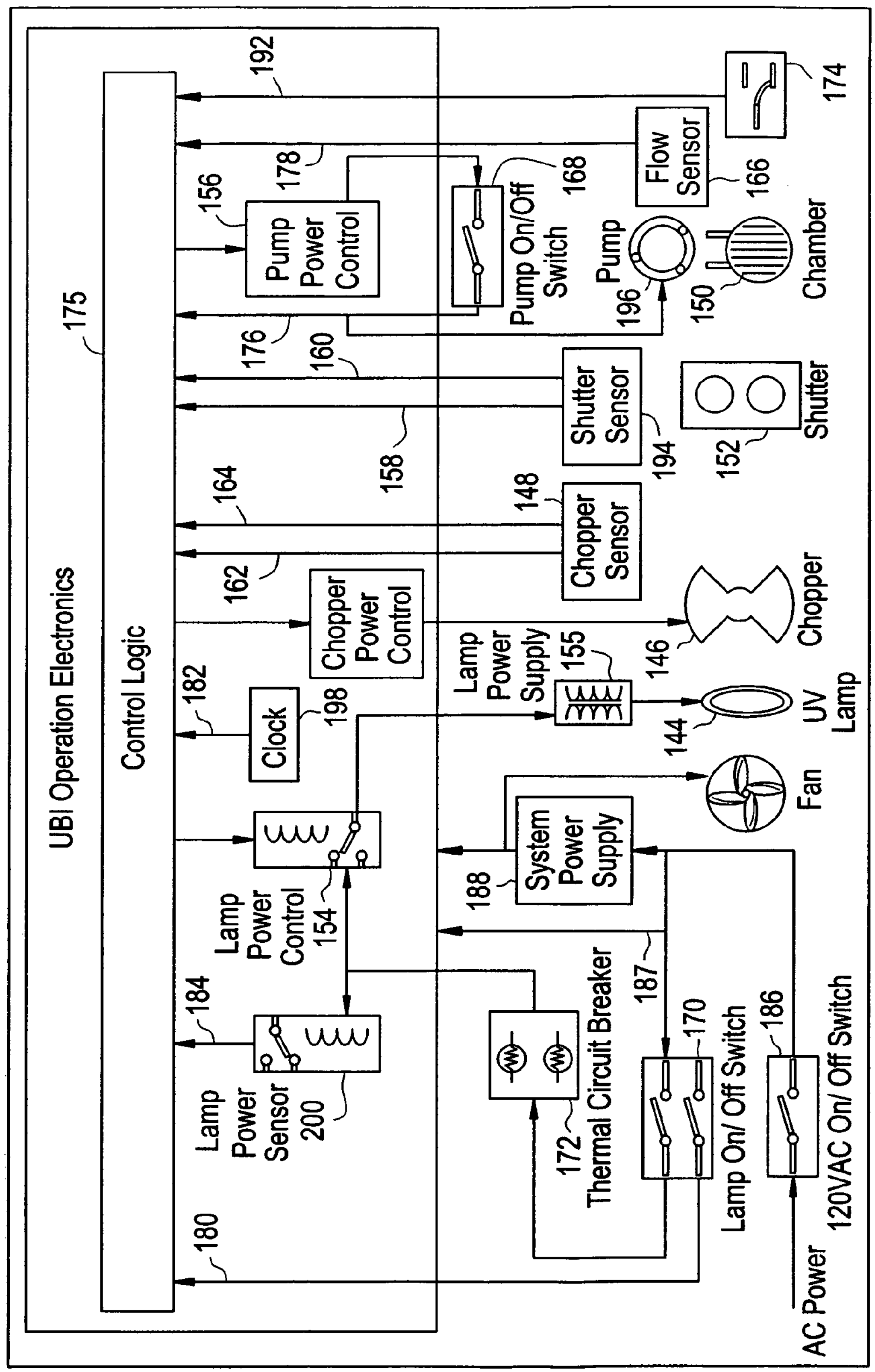
FIG. 16 is a block diagram of a blood irradiation system according to some embodiments of the present invention.

FIG. 16 depicts a block diagram of the above-described system and components thereof, as well as additional components for the control and/or monitoring of such components and the UBI system in general. Accordingly, UV lamp 144 emits a particular wavelength(s), which, after passing through chopper wheel assembly 146 and the aperture of shutter 152, enters exposure chamber 150. To accomplish this, preferably several conditions may be satisfied according to the system functions described by associating the components of FIG. 16 with the Operational States of FIG. 17.

State 1: A state in which either one or more (preferably all) of the following states occur:

chamber 150 is not inserted into the system,
shutter 152 is closed,
chopper wheel 146 is off,
UV lamp power control 154 is energized, and
pump power control 156 is energized.

State 2: A state in which either one or more (preferably all) of the following states occur:

chamber 150 is inserted into the system,
shutter 152 is closed,
chopper-wheel 146 is off,
UV lamp power control 154 is energized, and
pump power control 156 is energized.

State 3: A state in which either one or more (preferably all) of the following states occur:

chamber 150 is inserted into the system;
shutter 152 is open;
chopper-wheel 146 is on;
UV lamp power control 154 is energized; and
pump power control 156 is energized.

State 4: A state in which either one or more (preferably all) of the following states occur:

chamber 150 is inserted into the system,
shutter 152 is open, the chopper 146 is off,
UV lamp power control 154 is energized,
pump power control 156 is energized, and
either the pump On/Off switch 168 is off or the flow sensor 166 indicates No Flow.

Fail-Safe State: A state in which either one or more (preferably all) of the following states occur:

chamber 150 is inserted into the invention,
shutter 152 is open,
chopper 146 is in an unknown condition,
UV lamp power control 154 is de-energized, and
pump power control 156 is de-energized.

The following signal-sensory information (see *Fig.* 16) may be preferably used by the control logic to determine the appropriate state of operation.

| Signal Monitoring | FIG. 16 Item |
|---|---|
| 1-Shutter fully open sensor | 158 |
| 2-Shutter fully closed sensor | 160 |
| 3-Chopper first position sensor | 162 |
| 4-Chopper second position sensor | 164 |
| 5-Flow sensor | 166 |
| 6-Pump Switch | 168 |
| 7-Lamp Switch | 170 |
| 8-120VAC lamp thermal breaker | 172 |
| 9-Chamber position sensor | 174 |

Based upon the status of one or more of such signals, relevant system status information may be provided to the operator and/or monitoring system-e.g., computer. These status indicators, using audio and visual means, may fall into two modes: (1) an alert mode where an alert is provided to inform a operator of an operator procedural error, and (2) an alarm mode, which provides a highly visual and/or highly audible alarm of serious instrument hardware (and/or software) malfunction, which may cause the control logic 175 to force the instrument into a fail-safe condition.

| Alert Mode | Signal Item | Action |
|---|---|---|
| 1-No Flow and Shutter open | 176, 178, 160 | turn off chopper-wheel |
| 2-Lamp switch off and shutter open | 180, 160 | |
| 3-Shutter not fully open or fully closed | 158, 160 | |

| Alarm Mode | Signal Item | Action |
|---|---|---|
| 4-No Chopper motion and Shutter open | 162, 164, 160 | turn off lamp and pump |
| 5-System clock failure | 182 | turn off lamp and pump |
| 6-Thermal switch failure | 184 | turn off lamp |

In preferred embodiments of the invention, control logic 175 may determine the operational state of the invention at most (preferably) all times. For example, following power on of the instrument, in which AC switch 186 is activated, 120 VAC 187 (for example) is routed within the instrument to power supply 188, operation electronics and lamp On/Off switch 170. Thus, Control logic 175 preferably forces the operational condition to be in State 1.

Figure 17:
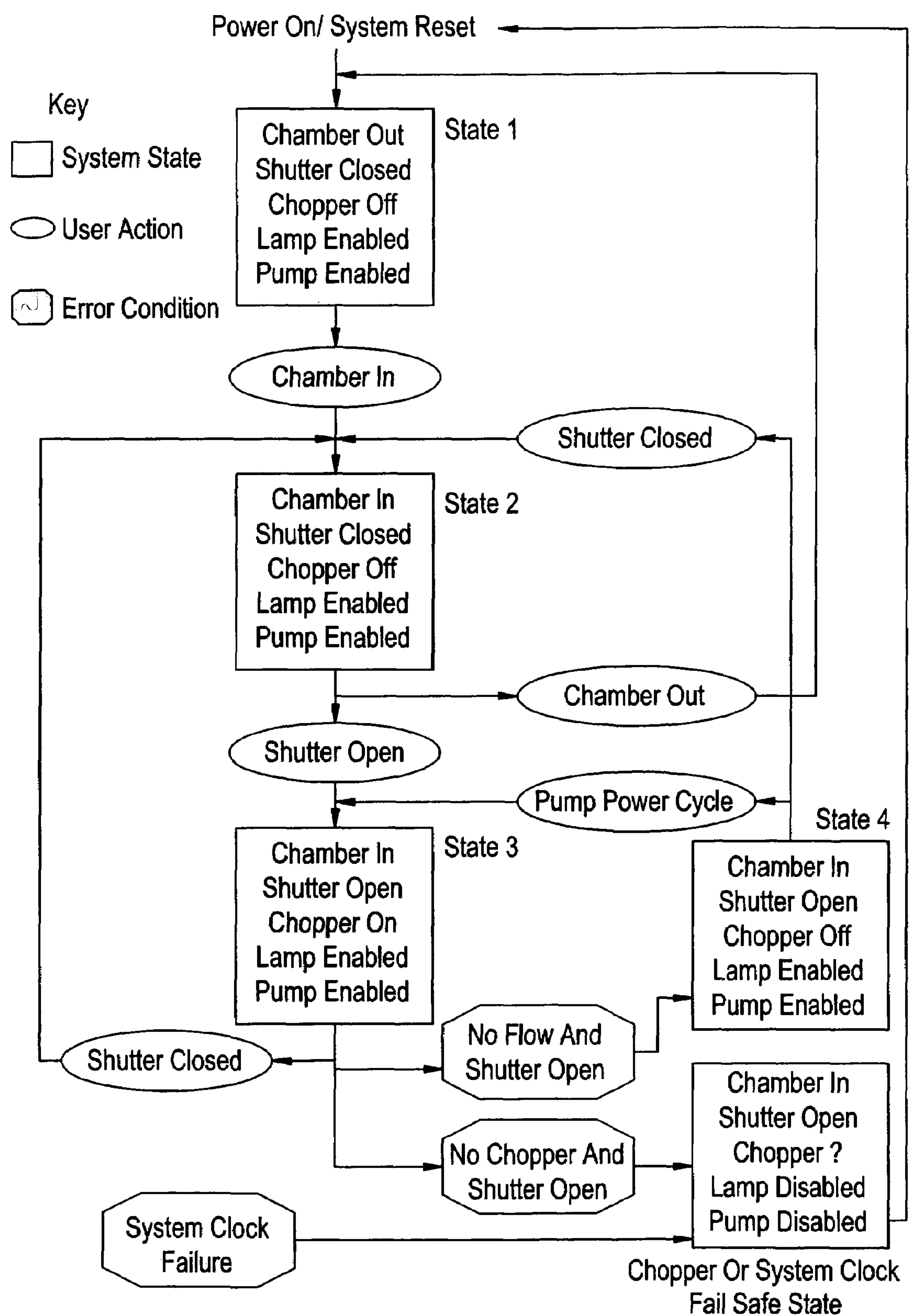
FIG. 17 is a flowchart of an operation of a blood irradiation system according to some embodiments of the present invention.

According to some embodiments of the present invention, as part of a normal medical procedure to expose a patient's blood to UV radiation, chamber 150 may first be inserted into the system. As seen in FIG. 17, the transition from State 1 to State 2 is initiated by the insertion of the exposure chamber 150 into the system. Chamber sensor 174 confirms its proper inserted position by sending signal 192 to the control logic 175, which in turn performs the change to State 2. Removing the chamber 150 from the system (i.e., chamber receiving housing) results in an immediate return to State 1.

To continue the process of blood irradiation, the aperture (shutter mechanism) 152 is opened by manual action of the instrument operator. This is preferably done to allow the chamber 150 contents to be exposed to the UV lamp 144 radiation. The transition from State 2 to State 3 may be initiated by this action of opening the aperture 152. Shutter sensor(s) 194 may determine whether the shutter 152 is fully closed or fully open, via signals 158 and 160. If the sensor 160 which senses a fully closed status of the aperture indicates that the aperture is not fully closed (i.e. the aperture is partially open), the control logic 175 forces the instrument to be in State 3. If sensor 158, which senses the aperture being fully opened, does not indicate a fully open state, then a simple alert (Alert Mode #3, as listed above) may be issued to inform the operator of the system that the aperture is partially open. Closing the aperture 152 fully may preferably cause the control logic 175 to force the instrument to return to State 2. It is important to note that if the chamber 150 is not inserted properly into the system at the start of the process, a safety feature of the aperture mechanism 152 preferably prevents the aperture from being opened (even partially), and hence transition from State 2 to State 3 is also thereby prevented.

As the medical procedure continues in State 3, the blood is preferably pushed through the chamber 150 by pump 196. To determine if this is occurring, the sensor166 monitors IV tubing for an indication of flow, and the status of pump switch 168 output is determined to establish whether the switch is in an 'on' or 'off' position. If either of these conditions determines that the blood is not moving through the chamber, a "no flow" condition is preferably declared. It is worth noting that such a "no flow" condition preferably results in the control logic 175 forcing a transition to State 4. Power cycling the pump (e.g., the pump switch 168 from on to off to on), preferably causes the control logic 175 to make a system transition back to State 3. Closing aperture 152 preferably causes the control logic 175 to make a system transition back to State 2.

While in State 3, the optical aperture interrupter chopper wheel 146 may be activated. When activated, the chopper wheel preferably rotates at a specific RPM. The rotation causes a periodic "on" and "off" timing characteristic to the chamber 150 irradiation. The wheel motion may be continuously measured by sensor 148, which preferably monitors two specific locations along the circumference of the wheel. In particular, sensor 148 may forward position signals 162 and 164 to the control logic 175. The timing of this wheel rotation is preferably measured to ensure a proper exposure time for the blood flowing through the chamber 150. If the chopper wheel 146 motion stops, the control logic 175 may receive signals 162 and/or 164 from sensor 148 indicating such failure. As a result, the control logic 175 may activate an alarm (Alarm Mode #4, as listed above) to notify the operator of hardware malfunction, and also preferably deactivate both the lamp power control 154 and the pump power control 156. If sensor 148 malfunctions, chopper wheel 146 motion cannot be determined. In this failure situation also, the control logic 175 may activate an alarm (Alarm Mode #4, as listed above) and deactivate both the lamp power control 154 and the pump power control 156. These two failure conditions preferably cause the control logic 175 to force the instrument into the fail-safe state. In preferred embodiments, one way to escape from this state is to remove power to the instrument by deactivating AC Switch 186, and repair the failed item.

Also in some of the preferred embodiments, as an additional safety feature, the control logic 175 ensures that the chopper wheel 146 rests in a specific physical orientation —blocking the optical aperture between the lamp 144 and the chamber 150, when it is parked in its stopped position. Such a parking orientation may be forced whenever the instrument is in State 1, 2, or 4 (for example). This feature provides a secondary back-up to the aperture 152, to protect the operator and/or patient from accidental UV exposure, if that mechanism is improperly forced open without the use of the specified exposure chamber 38 (for example).

In some embodiments of the invention, in all States of operation, the control logic 175 monitors the system for the occurrence of two particular types of failures. First, the control logic monitors the system for a failure of the internal system timing clock 198. Such a failure may cause the control logic 175 to initiate an immediate transition of the instrument into the fail-safe state. In particular, the Control Logic 175 may activate an alarm (Alarm Mode #5, as listed above) and deactivate both the lamp power control 154 and the pump power control 156. The second type of failure may be an overheat event which causes thermal circuit breaker 172 to "open", thereby removing AC power from the lamp power sensor 200 and from the lamp power supply 155. In such a failure situation, the instrument may not be able to illuminate the lamp 144, and may then be un-powered, and repaired. An alarm (Alarm Mode #6, as listed above) condition may then notify the operator of this status.

Accordingly, the above embodiments enable blood (and/or other fluids) to be safely and effective irradiated. Such embodiments may be used to irradiate blood according to the following exemplary protocol. For example, subjects undergo one or more sessions of (preferably) five ultraviolet blood irradiation treatments over a three-week period.

Treatment #1 Start;
Treatment #2, within 48 hours of the prior treatment;
Treatment #3, within 72 hours of the prior treatment;
Treatment #4, within five (5) days of the prior treatment; and
Treatment #5, within five (5) days of the prior treatment.

Sample Treatment Schedule

| | Sunday | Monday | Tuesday | Wed. | Thursday | Friday | Saturday |
|---|---|---|---|---|---|---|---|
| Week 1 | | | | Treatment 1 | | Treatment 2 | |
| Week 2 | | Treatment 3 | | | | | Treatment 4 |
| Week 3 | | | | | Treatment 5 | | |

The treatment may be accomplished by introducing a standard 20 gauge intravenous catheter into the patient's vein, and 1.5 cc of blood per pound of body weight is withdrawn according to the following formula: A=KW, where K is a constant (1.5 cc), and W is the patient's body weight in pounds. Preferably, the total amount of blood withdrawn should not exceed 250 ml in total.

The blood may be collected into a vacuum container prepared with 3000 to 5000 units of heparin sodium. The container is carefully inverted to mix the blood with the heparin, and then may be hung from an IV pole attached to the UBI system. The blood is then circulated through the exposure chamber, thereby exposing the blood to UV radiation. (e.g., UVC at between about 200 nm and about 400 nm), at a rate of approximately 30 ml/minute, before being returned to the patient.

The irradiated blood may then be returned to the patient at the fasted infusion rate allowed (per a standard administration set). A typical duration of the procedure is approximately 20 minutes.

Other embodiments of the invention may include systems for diagnostic applications with or without the use of a drug. For example, a predetermined therapy using one or another of the above disclosed system/device embodiments simulates the immune system, which initially seeks out blood borne pathogens and inflammation. A blood test at a predetermined time later may reveal and contribute to a diagnostic process. In addition, such a therapy may exacerbate an inflammatory reaction of a low grade and or an undetectable infection, which can be sighted using imaging devices, blood tests and patient feedback.

While certain embodiments of the present invention have been herein described, such descriptions have been provided as examples only and not as limitations to the invention. Accordingly, as one of ordinary skill in the art will appreciate, numerous other embodiments, some with additional or less features, are within the scope of this invention, a few embodiments of which are hereinafter claimed.

What is claimed is:

1. A blood irradiation system comprising:

an ultraviolet UV source providing a predetermined wavelength of radiation to provide a detrimental effect to virus and/or bacteria;

an exposure chamber for exposing a volume of blood to radiation;

a conduit between the UV source and the exposure chamber for passing UV radiation from the UV source to the exposure chamber;

a pump for pumping blood at a predetermined flow rate through the exposure chamber and between a first location and a second location; and a shutter assembly provided between the UV source and the exposure chamber and having a rotating disc having one or more spaced apart openings, each of the openings capable of being rotated to correspond to at least a portion of a first aperture in the fixed open position such that upon the first aperture being in an open position, UV radiation may pass through the conduit upon one of the openings of the one or more openings of the disc aligning with the open position of the first aperture;

wherein the shutter assembly is configured to provide a synchronous time-metered irradiation of the blood in the exposure chamber, the synchronous time-metered irradiation is configured to be based on the predetermined flow rate of the blood through the exposure chamber.

2. The system according to claim 1, wherein the exposure chamber includes one or more protuberances.

3. The system according to claim 2, wherein the protuberances inflict a particular fluidic turbulence upon a flow of blood in the chamber.

4. The system according to claim 3, wherein the protuberances ensure substantial irradiation of blood flowing through the chamber resulting from exposure to radiation.

5. The system according to claim 1, wherein the shutter assembly alternately opens and closes between the exposure chamber and the ultraviolet source thereby irradiating the material contained in the exposure chamber.

6. The system according to claim 1, further comprising a cooling plenum.

7. The system according to claim 6, wherein the cooling plenum includes an air inlet, a filter, a duct, a fan and an outlet.

8. The system according to claim 1, further comprising a control system for controlling operation of the system.

9. The system according to claim 1, further comprising at least one thermal sensor.

10. The system according to claim 9, wherein the thermal sensor comprises a thermal circuit breaker for controlling power supply to the ultraviolet radiation source.

11. The system according to claim 9, wherein the thermal sensor comprises a thermister.

12. The system according to claim 11, wherein the output of thermister is monitored by a control system, wherein upon the thermister sensing a predetermined temperature, the control system turns off power to the ultraviolet source.

13. The system according to claim 1, wherein the shutter assembly provides repeated opening and closing of a passage between the ultraviolet source and the exposure chamber.

14. The system according to claim 1, wherein the shutter assembly includes a first shutter having a fixed open position and a fixed closed position and a second shutter which is repeatedly opened and closed according to a predetermined timing.

15. The system according to claim 14, wherein the second shutter includes the rotating disc.

16. The system according to claim 15, wherein the rotating disc comprises a bow-tie shape.

17. The system according to claim 1, further comprising an administration set.

18. The system according to claim 15, wherein the shutter assembly includes a parking mechanism such that upon shutdown of the system, the rotating disc automatically stops in a position such that none of the openings of the rotating disc overlap with the first aperture.

19. The system according to claim 15, further comprising an exposure chamber housing for receiving the exposure chamber, a UV source power control, and a pump power control.

20. The system according to claim 19, further comprising a control logic means including a plurality of operational states.

21. The system according to claim 20, wherein the operational states include at least one of an operational state, an alert state, and an alarm state.

22. The system according to claim 21, wherein the operational states include at least one of a first state, a second state, and a third state.

23. The system according to claim 22, wherein the first state includes a state in which the exposure chamber is not received in the chamber exposure housing, the first shutter is closed, the second shutter is inactive, the UV source power control is active and the pump power control is active.

24. The system according claim 22, wherein second state includes the exposure chamber being received in the chamber exposure housing, the first shutter is closed, the second shutter is inactive, the UV source power control is active and the pump power control is active.

25. The system according to claim 22, wherein the third state includes the exposure chamber is inserted into the exposure chamber housing, the first shutter is open, the second shutter is active, the UV source power control is active, and the pump power control is active.

26. The system according to claim 21, wherein the alert state includes the exposure chamber being received in the exposure chamber housing, the first shutter is open, the second shutter is inactive, the UV source power control is active, the pump power control is active, and either a pump on/off switch is in the off position or a flow sensor indicates substantially no flow.

27. The system according to claim 22, wherein the alarm state includes the exposure chamber being received in the exposure chamber housing, the first shutter is open, a status of the second shutter is unknown, the UV source power control is inactive and the pump power control is inactive.

28. The system according to claim 21, further comprising a visual and/or audible indication means for indicating the alert and/or alarm state.

29. A blood irradiation system comprising:

an ultraviolet UV source providing a predetermined wavelength of radiation to provide a detrimental effect to virus and/or bacteria;

an exposure chamber for exposing a volume of blood to radiation including one or more protuberances to impart a particular fluidic turbulence upon a flow of blood within the chamber;

a conduit between the UV source and the exposure chamber for passing UV radiation from the UV source to the exposure chamber;

a pump for pumping blood at a predetermined flow rate through the exposure chamber and between a first location and a second location; and a shutter assembly provided between the UV source and the exposure chamber, wherein the shutter assembly includes a first shutter having a fixed open position and a fixed closed position and a second shutter which is repeatedly opened and closed according to a predetermined timing, wherein the second shutter includes a rotating disc having one or more spaced apart openings, each of the openings capable of being rotated to correspond to at least a portion of a first aperture in the fixed open position such that upon the first aperture being in an open position, UV radiation may pass through the conduit upon one of the openings of the one or more openings of the disc aligning with the open position of the first aperture;

wherein the shutter assembly is configured to provide a synchronous time-metered irradiation of the blood in the exposure chamber, the synchronous time-metered irradiation is configured to be based on the predetermined flow rate of the blood through the exposure chamber;

a cooling plenum comprising an air inlet, a filter, a duct, a fan and an outlet;

a control system for controlling operation of the system; and at least one thermal sensor comprising a thermal circuit breaker for controlling power supply to the ultraviolet radiation source.

30. A shutter assembly for a blood processing system having a blood exposure chamber for exposing blood to an ultraviolet ("UV") radiation, comprising:

a rotating disc having one or more spaced apart openings, each of the openings capable of being rotated to correspond to at least a portion of a first aperture of the blood exposure chamber in a fixed open position such that upon the first aperture being in an open position, the UV radiation may pass through the shutter assembly upon one of the openings of the one or more openings of the disc aligning with the open position of the first aperture;

the rotating disc configured to provide a synchronized time-metered exposure of the blood flowing through the blood exposure chamber to the UV radiation through at least a portion of the first aperture and one or more spaced apart openings of the rotating disc.

31. The assembly according to claim 30, wherein the shutter assembly includes a parking mechanism such that upon shutdown of the system, the rotating disc automatically stops in a position such that none of the openings of the rotating disc overlap with the first aperture.

* * * * *